US005962259A

United States Patent [19]
Hodgson et al.

[11] Patent Number: 5,962,259
[45] Date of Patent: Oct. 5, 1999

[54] RESPONSE REGULATOR POLYNUCLEOTIDES

[75] Inventors: John Edward Hodgson, Malvern; Nicola Gail Wallis, Wayne, both of Pa.

[73] Assignee: SmithKline Beecham plc, United Kingdom

[21] Appl. No.: 08/771,783

[22] Filed: Dec. 20, 1996

[30] Foreign Application Priority Data

Dec. 22, 1995 [GB] United Kingdom .................... 9526332
Dec. 22, 1995 [GB] United Kingdom .................... 9526358
Dec. 22, 1995 [GB] United Kingdom .................... 9526361

[51] Int. Cl.[6] ............................. C12N 1/21; C12N 5/10; C12N 15/31
[52] U.S. Cl. ................... 435/69.1; 435/320.1; 435/325; 435/252.3; 435/455; 435/471; 536/23.7; 536/24.3
[58] Field of Search ............................... 435/69.1, 172.3, 435/320.1, 325, 252.3, 254.11, 455, 471; 536/23.7, 24.3

[56] References Cited

U.S. PATENT DOCUMENTS 5,476,781 12/1995 Moyer et al. ......................... 435/240.2
5,602,014 2/1997 Mizumura et al. ..................... 435/129
5,606,022 2/1997 Rasmussen .............................. 530/350

FOREIGN PATENT DOCUMENTS

WO 92/17785 10/1992 WIPO .......................... G01N 33/569

OTHER PUBLICATIONS

Benjamini et al., Immunology: A Short Course, second ed., Wiley–Liss, New York, p. 40, 1992.
Daniel et al., Virology 202:540–549, 1994.
Ishizuka et al. A putative two–component regulatory system involved in secondary metabolism in Streptomyces spp. Journal of Bacteriology. vol. 174, No. 23, pp. 7585–7594, Dec. 1992.
Lee et al. Phosphate regulon in members of the family Enterobacteriaceae: comparison of the phoB–phoR operons of *Escherichia coli*, *Shigella dysenteriae*, and *Klebsiella pneumoniae*. Journal of Bacteriology. vol. 171, No. 12, pp. 6593–6599, Dec. 1989.
Makino et al. Nucleotide sequence of the phoB gene, the positive regulatory gene for the phosphate regulon of *Escherichia coli* K12. Journal of Molecular Biology. vol. 190, pp. 37–44, 1986.
Sambrook et al. MOlecular Cloning: A Laboratory Manual, 2d ed. CSHLP, Cold Spring Harbor, NY. Chapters 9 and 11, 1989.
Scholten et al. The pho regulon of Shigella flexneri. Molecular Miobiology. vol. 15, No. 2, pp. 247–254, 1995.
Stock et al. Signal Transduction in bacteria. Nature. vol. 344, pp. 395–400, Mar. 29, 1990.
Stock et al., Protein phosphorylation and regulation of adaptive responses in bacteria. Microbiological Reviews. vol. 53, No. 4, pp. 450–490, Dec. 1989.
Wells. Additivity of mutational Effects in Proteins. Biochemistry. vol. 29, No. 37, pp. 8509–8517, Sep. 18, 1990.

George et al. Current Methods in sequence comparison and analysis. Macromolecular Sequencing and Synthesis. Alan R Liss, Inc. pp. 127–149, 1988.
Zhang et al. A bacillus subtilis bglA gene encoding phospho–β–glucosidase is inducible and closely linked to a NADH dehydrogenase–encoding gene. Gene. vol. 140, pp. 85–90, 1994.
Kessler et al. Plant Molecular Biology. vol. 18, No. 4, p. 177, 1992.
Seki et al., "Cloning and Nucleotide Sequence of phoP, the Regulatory Gene for Alkaline Phosphatase and Phosphodiesterase in *Bacillus subtilis*", *Journal of Bacteriology*, 169, No. 7, pp. 2913–2916(1987).
Hulett et al., "Sequential Action of Two–Component Genetic Switches Regulates the PHO Regulon in *Bacillus subtilis*", *Journal of Bacteriology*, 176, No. 5, pp. 1348–1358.
Bayles et al. "The use of degenerate, sensor gene–specific, oligodeoxyribonucleotide primers to amplify DNA fragments from *Staphylococcus aureus*", *Gene*, 123, pp. 99–103 (1993).
Volz et al., "Stuctural Conversation in the CheY Superfamily", *Biochemistry*, 32, No. 44, pp. 11741–11753 (1993).
Feher et al., $^1$H, $^{15}$N, and $^{13}$C backbone chemical shift assignments, secondary structures, and magnesium–binding characteristics of the *Bacillus subtilis* response regluator, SpoOF, determined by heteronuclear high–resolution NMR, *Protein Science*, 4, pp. 1801–1814 (1995).
Volkman et al., Three–Dimensional Solution Structure of the N–Terminal Receiver Domain of NTRC, *Biochemistry*, 34, pp. 1413–1424 (1995).
Swanson, et al., "Histidine and aspartate phosphorylation: two–component systems and the limits of homology", *TIBS*, 19, pp. 485–491 (1994).
Stock, et al., "Three–dimensional structure of CheY the response regulator of bacterial chemotaxis", *Nature*, 337, pp. 745–749 (1989).
Volz, et al., "Crystal Structure of *Escherichia coli* CheY Refined at 1.7–a Resolution", *The Journal of Biological Chemsitry*, 266, No. 23, pp. 15511–15519 (1991).
Matsumura, P., et al., *J. Bacteriol.*, 160, pp. 36–41 (1984).
Turgay, et al., The gtcRS operon coding for two–component system regulatory proteins is located adjacent to the grs operon of *Bacillus brevis*, DNA Sequence–The Journal of Sequencing and Mapping, (1995), vol. 5: pp. 283–290.

*Primary Examiner*—Elizabeth Kemmerer
*Attorney, Agent, or Firm*—Edward R. Gimmi; William T. King; Arthur E. Jackson

[57] ABSTRACT

Novel response regulator polypeptides and DNA (RNA) encoding such polypeptides and a procedure for producing such polypeptides by recombinant techniques is disclosed. Also disclosed are methods for utilizing such polynucleotides and polypeptides for the treatment of infection, particularly bacterial infections. Antagonists against such the polypeptides of the invention and their use as a therapeutic to treat infections, particularly bacterial infections are also disclosed. Also disclosed are diagnostic assays for detecting diseases related to the presence the nucleic acid sequences and the polypeptides of the invention in a host. Also disclosed are diagnostic assays for detecting polynucleotides encoding response regulators and for detecting the polypeptide in a host.

21 Claims, 2 Drawing Sheets

FIGURE 1

```
  1 AATGCACTAA ATAAAATAAC CGTAATGGAA TAAATCGCAA TTCTAGCATA
 51 GAGTGTTTTA AACATGATTC TCCACCTTAT AGCCTTGTCC TCTTACTGTG
101 TCAATTGTAA GTGTGGCATT TAATTTTTTT AATCTTTGGC GTAGTCGCTT
151 AATATGAACG TCAACTGTTC GTTCATCTCC TTCATAATCA TAGCCCCAAA
201 TTTTTTCTAT TATTTGTTCA CGAGTAAAGA TTTGCTTAGG ACGTGCTGCA
251 AGCATAAATA ATAATTGAAA TTCCTTGTTC GGTAACGTCA TCGTTTTATT
301 AGATACTTGG AGTTCCAAAT AGGATTGGTT TAGCGTTAAG TTGCCAATAG
351 TCATTTCTGA ATTTGAATTG ATATTATATC GACGTAATAC CGCACGANTT
401 CTAAAAATAA GTTCCTTAAC CTCAAAGGGT TTGGTTACAT AATCGTCAGT
451 ACCACTTATA AACGCACGCT CTTTGTCACT AAGTGCATCC CGCGCTGTTA
501 ACATAATAAC TGGTATATCA TAATCATTTT TTAATGTATT ACATAATTGA
551 AAGCCGTCCA TACCATCCAT CATAATATCT ACCACTGCAA TATCGACACG
601 CTGTTTTTCT AAAAGTTTTA ATGCAGCTTC ACCACTTGGT TGTGTGTATG
651 CATCAATGTG CTCTGTTTGT AAATGGCTAG CTATATAATT TAGGATTCGA
701 GGATCGTCAT CGACAACAAG ACATTGCACC ATAGCTATAA ACTCCCTTAT
751 CTTTTTCATT TATTATACAT GTAAAATATT TTTGGGTAAA AAAACAATGG
801 TTCATATTGA GTTCATATTT CAACCCTTAT ACTTGACGCT AAAGAAGAAA
```

FIGURE 2

```
  1 MKKIREFIAM VQCLVVDDDP RILNYIASHL QTEHIDAYTQ PSGEAALKLL
 51 EKQRVDIAVV DIMMDGMDGF QLCNTLKNDY DIPVIMLTAR DALSDKERAF
101 ISGTDDYVTK PFEVKELIFR IRAVLRRYNI NSNSEMTIGN LTLNQSYLEL
151 QVSNKTMTLP NKEFQLLFML AARPKQIFTR EQIIEKIWGY DYEGDERTVD
201 VHIKRLRQRL KKLNATLTID TVRGQGYKVE NHV
```

RESPONSE REGULATOR POLYNUCLEOTIDES

This application claims the benefit of GB Application No. 9526332.3, filed Dec. 22, 1995, GB Application No. 9526358.8, filed Dec. 22, 1995, and GB Application No. 9526361.2, filed Dec. 22, 1995.

FIELD OF THE INVENTION

This invention relates generally to newly identified polynucleotides and polypeptides in the family of the PhoP response regulatory protein from *Bacillus subtilis*.

BACKGROUND OF THE INVENTION

Many two component signal transduction systems (TCSTS) have been identified in bacteria (Stock, J. B. et al., (1989) *Microbiol. Rev.*, 53, 450–490). These are involved in the bacterium's ability to monitor its surroundings and adapt to changes in its environment. Several of these bacterial TCSTS are involved in virulence and bacterial pathogenesis within the host. Response regulators are components of the TCSTS. These proteins are phosphorylated by histidine kinases and once phosphorylated effect the response, often through a DNA binding domain becoming activated. The response regulators are characterized by a conserved N-terminal domain of approximately 100 amino acids. The N-terminal domains of response regulators as well as retaining five functionally important residues, corresponding to the residues D12, D13, D57, T87, K109 in CheY (Matsumura, P. et al., (1984) *J. Bacteriol.* 160, 36–41), have conserved structural features (Volz, K. (1993) *Biochemistry* 32, 11741–11753). The 3-dimensional structures of CheY from *Salmonella typhirnurium* (Stock, A. M. et al., (1989) *Nature*, 337, 745–749) and *Escherichia coli* (Volz, K. & Matsumura, P. (1991) *J. Biol. Chem.* 266, 15511–15519) and the N-terminal domain of nitrogen regulatory protein C from *S. typhimurium* (Volkman, B. F. et al., (1995) *Biochemistry*, 34, 1413–1424), are available, as well as the secondary structure of SpoOF from *Bacillus subiilis* (Feher, V. A. etal., (1995) *Protein Science*, 4, 1801–1814). These structures have a (a/b)$_5$ fold. Several structural residues are conserved between different response regulator sequences, specifically hydrophobic residues within the b-sheet hydrophobic core and sites from the a-helices. This family of response regulators includes PhoP. PhoP is the response regulator of the Pho TCSTS which is involved in the regulation of alkaline phosphatase genes (Seki, T. et al., (1987) *J. Bacteriol*, 169, 2913–2916).

Histidine kinases are components of the TCSTS which autophosphorylate at a histidine residue. The phosphate group is then transferred to the cognate response regulator. The histidine kinases have five short conserved amino acid sequences (Stock, J. B. et al., *Microbiol. Rev.* 53, 450–490; Swanson, R. V. et al., (1994) *TIBS*, 19, 485–491). These are the histidine residue, which is phosphorylated, followed by a conserved asparagine residue after approximately 100 residues. After another 15 to 45 residues a DXGXG motif is found, followed by a FXXF motif after another 10–20 residues. Ten to twenty residues further on another glycine motif, GXG is found. The two glycine motifs are thought to be involved in nucleotide binding.

Among the processes regulated by TCSTS are production of virulence factors, motility, antibiotic resistance and cell replication. Inhibitors of TCSTS proteins would prevent the bacterium from establishing and maintaining infection of the host by preventing it from producing the necessary factors for pathogenesis and thereby have utility in anti-bacterial therapy.

Clearly, there is a need for factors that may be used to screen compounds for antibiotic activity and which may also be used to determine their roles in pathogenesis of infection, dysfunction and disease. There is a need, therefore, for identification and characterization of such factors which can play a role in preventing, ameliorating or correcting infections, dysfunctions or diseases.

SUMMARY OF THE INVENTION

Toward these ends, and others, it is an object of the present invention to provide polypeptides, inter alia, that have been identified as novel peptides by comparison between the amino acid sequence set out in FIG. 2 and known amino acid sequences of other proteins such as PhoP protein.

It is a further object of the invention, moreover, to provide polynucleotides that encode the novel polypeptides of the invention.

In a particularly preferred embodiment of this aspect of the invention, the polynucleotide comprises the region encoding the novel polypeptides in the sequence set out in FIG. 1 [SEQ ID NO:1], or a fragment, analogue or derivative thereof.

In another particularly preferred embodiment of the present invention there is a novel protein from *Staphylococcus aureus* comprising the amino acid sequence of FIG. 2 [SEQ ID NO:2], or a fragment, analogue or derivative thereof.

In accordance with this aspect of the present invention there is provided an isolated nucleic acid molecule encoding a mature polypeptide expressible by the *Staphylococcus aureus* DNA contained in the National Collection of Industrial and Marine Bacteria Ltd. (NCIMB), Aberdeen, Scotland under number NCIMB 40771 on Sep. 11, 1995.

In accordance with this aspect of the invention there are provided isolated nucleic acid molecules encoding novel polypeptides, including mRNAs, cDNAs, genomic DNAs and, in further embodiments of this aspect of the invention include biologically, diagnostically, prophylactically, clinically or therapeutically useful variants, analogs or derivatives thereof, or fragments thereof, including fragments of the variants, analogs and derivatives, and compositions comprising same.

In accordance with another aspect of the present invention, there is provided the use of a polynucleotide of the invention for therapeutic or prophylactic purposes, in particular genetic immunization.

Among the particularly preferred embodiments of this aspect of the invention are naturally occurring allelic variants of the novel nucleic acid sequences and polypeptides encoded thereby.

In accordance with this aspect of the invention there are provided a novel polypeptide characterized by the amino acid sequence of SEQ ID NO:2, as well as biologically, diagnostically, prophylactically, clinically or therapeutically useful fragments, variants and derivatives thereof, variants and derivatives of the fragments, and analogs of the foregoing, and compositions comprising same.

Among the particularly preferred embodiments of this aspect of the invention are variants of the polypeptide encoded by naturally occurring alleles of the gene of the invention, which is characterized by the nucleic acid sequences of SEQ ID NO:1.

In a preferred embodiment of this aspect of the invention there are provided methods for producing the aforementioned polypeptides.

In accordance with yet another aspect of the present invention, there are provided inhibitors to such polypeptides, useful as antibacterial agents, including, for example, antibodies.

In accordance with certain preferred embodiments of this aspect of the invention, there are provided products, compositions and methods, inter alia: assessing expression; to treat and prevent bacterial infections; assaying genetic variation; and administering a novel polypeptide or polynucleotide of the invention to an organism to raise an immunological response against bacteria, especially Staphylococcus.

In accordance with certain preferred embodiments of this and other aspects of the invention there are provided polynucleotides that hybridize to the novel polynucleotide sequences of the invention, including SEQ ID NO:1 .

In certain additional preferred embodiments of this aspect of the invention there are provided antibodies against the polypeptides of the invention.

In accordance with another aspect of the present invention, there are provided agonists to the polynucleotides and/or polypeptides of the invention which are also preferably bacteriostatic or bacteriocidal.

In accordance with yet another aspect of the present invention, there are provided antagonists to the polynucleotides and/or polypeptides of the invention which are also preferably bacteriostatic or bactericidal.

In a further aspect of the invention there are provided compositions comprising a polynucleotide or a polypeptide of the invention for administration to a cell or to a multicellular organism.

Various changes and modifications within the spirit and scope of the disclosed invention will become readily apparent to those skilled in the art from reading the following description and from reading the other parts of the present disclosure.

This invention relates generally to newly identified polynucleotides and polypeptides of the response regulator, and more particularly the PhoP family. Also encompassed by this invention are variants and derivatives of these polynucleotides and polypeptides; processes for making these polynucleotides and these polypeptides, and their variants and derivatives; agonists and antagonists of the polypeptides; and uses of these polynucleotides, polypeptides, variants, derivatives, agonists and antagonists.

In particular, the invention relates to a novel response regulator protein from *Staphylococcus aureus* WCUH29, characterized in that it comprises the amino acid sequence given in SEQ ID NO: 2 or a fragment, analogue or derivative thereof.

In accordance with another aspect of the present invention, there are provided polynucleotides (DNA or RNA) which encode such polypeptides.

BRIEF DESCRIPTION OF THE DRAWINGS

The following drawings depict certain embodiments of the invention. They are illustrative only and do not limit the invention otherwise disclosed herein.

FIG. 1 provides the nucleic acid sequences [SEQ ID NO:1] of the gene of the invention.

FIG. 2 provides the amino acid sequences [SEQ ID NO:2] of a polypeptide of the invention.

GLOSSARY

The following illustrative explanations are provided to facilitate understanding of certain terms used frequently herein, particularly in the Examples. The explanations are provided as a convenience and are not limitative of the invention.

BINDING MOLECULE, as used herein, refers to molecules or ions which bind or interact specifically with the polypeptides or polynucleotides of the present invention, including, for example enzyme substrates, cell membrane components and classical receptors. Binding between polypeptides of the invention and such molecules, including binding or interaction molecules may be exclusive to polypeptides of the invention, which is preferred, or it may be highly specific for polypeptides of the invention, which is also preferred, or it may be highly specific to a group of proteins that includes polypeptides of the invention, which is preferred, or it may be specific to several groups of proteins at least one of which includes a polypeptide of the invention. Binding molecules also include antibodies and antibody-derived reagents that bind specifically to polypeptides of the invention.

GENETIC ELEMENT generally means a polynucleotide comprising a region that encodes a polypeptide or a polynucleotide region that regulates replication, transcription or translation or other processes important to expression of the polypeptide in a host cell, or a polynucleotide comprising both a region that encodes a polypeptide and a region operably linked thereto that regulates expression. Genetic elements may be comprised within a vector that replicates as an episomal element; that is, as a molecule physically independent of the host cell genome. They may be contained within plasmids. Genetic elements also may be comprised within a host cell genome; not in their natural state but, rather, following manipulation such as isolation, cloning and introduction into a host cell in the form of purified DNA or in a vector, among others.

A cell has been TRANSFORMED by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cells containing the exogenous DNA.

HOST CELL is a cell which has been transduced, transformed or transfected, or is capable of transformation or transfection by an exogenous polynucleotide sequence.

A CLONE is a population of cells derived from a single cell or common ancestor by mitosis. A CELL LINE is a clone of a primary cell that is capable of stable growth in vitro for many generations.

REPLICON is any genetic element (e.g., plasmid, chromosome, virus) that functions as an autonomous unit of DNA replication in vivo; i.e., capable of replication under its own control.

VECTOR is a replicon, such as a plasmid, phage, or cosmid, to which another DNA segment may be attached so as to bring about the replication of the attached segment.

DOUBLE-STRANDED DNA MOLECULE refers to the polymeric form of deoxyribonucleotides (bases adenine, guanine, thymine, or cytosine) in a double-stranded helix, both relaxed and supercoiled. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA CODING SEQUENCE OF or a NUCLEOTIDE SEQUENCE ENCODING a particular protein, is a DNA sequence which is transcribed and translated into a polypeptide when placed under the control of appropriate regulatory sequences.

PROMOTER SEQUENCE is a DNA regulatory region capable of binding RNA polymerase in a cell and initiating transcription of a downstream (3' direction) coding sequence. For purposes of defining the present invention, the promoter sequence is bound at the 3' terminus by a translation start codon (e.g., ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the -10 and -35 consensus sequences.

DNA CONTROL SEQUENCES refers collectively to promoter sequences, ribosome binding sites, polyadenylation signals, transcription termination sequences, upstream regulatory domains, enhancers, and the like, which collectively provide for the expression (i.e., the transcription and translation) of a coding sequence in a host cell. A control sequence directs the expression of a coding sequence in a cell when RNA polymerase will bind the promoter sequence and transcribe the coding sequence into mRNA, which is then translated into the polypeptide encoded by the coding sequence.

DIGESTION of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment. Size separation of the cleaved fragments is performed using 8 percent polyacrylamide gel described by Goeddel, D. et al., (1980) *Nucleic Acids Res.*, 8, 4057.

A HETEROLOGOUS region of a DNA construct is an identifiable segment of DNA within or attached to another DNA molecule that is not found in association with the other molecule in nature.

IDENTITY or SIMILARITY, as known in the art, are relationships between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. Both identity and similarity can be readily calculated (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity and similarity between two polynucleotide or two polypeptide sequences, both terms are well known to skilled artisans (*Sequence Analysis in Molecular Biology*, von Heinje, G., Academic Press, 1987; *Sequence Analysis Primer*, Gribskov, M. and Devereux, J., eds., M Stockton Press, New York, 1991; and Carillo, H., and Lipman, D., (1988) *SIAM J. Applied Math.*, 48, 1073. Methods commonly employed to determine identity or similarity between sequences include, but are not limited to those disclosed in Carillo, H., and Lipman, D., (1988) *SIAM J. Applied Math.*, 48, 1073. Preferred methods to determine identity are designed to give the largest match between the sequences tested. Methods to determine identity and similarity are codified in computer programs. Preferred computer program methods to determine identity and similarity between two sequences include, but are not limited to, GCG program package (Devereux, J., et al., (1984) *Nucleic Acids Research* 12(1), 387), BLASTP, BLASTN, and FASTA (Atschul, S. F. et al., (1990) *J. Molec. Biol.* 215, 403).

ISOLATED means altered "by the hand of man" from its natural state; i.e., that, if it occurs in nature, it has been changed or removed from its original environment, or both. For example, a naturally occurring polynucleotide or a polypeptide naturally present in a living organism in its natural state is not "isolated", but the same polynucleotide or polypeptide separated from the coexisting materials of its natural state is "isolated", as the term is employed herein. As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

POLYNUCLEOTIDE(S) generally refers to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. Polynucleotides embraces short polynucleotides often referred to as oligonucleotide(s).

LIGATION refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 μg of approximately equimolar amounts of the DNA fragments to be ligated.

POLYPEPTIDES, as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature. Several particularly common modifications, glycosylation, lipid attachment, sulfation, gammacarboxylation of glutamic acid residues, hydroxylation and ADP-ribosylation, for instance, are described in most basic texts, such as, for instance *PROTEINS—STRUCTURE AND MOLECULAR PROPERTIES*, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in *POSTTRANSLATIONAL COVALENT MODIFICATION OF PROTEINS*, B. C. Johnson, Ed., Academic Press, New York (1983); Seifter et al., (1990) *Meth. Enzymol.* 182, 626–646 and Rattan et al., "Protein Synthesis: Posttranslational Modifications and Aging", (1992) *Ann. N.Y. Acad. Sci.* 663, 48–62. It will be appreciated, as is well known and as noted above, that polypeptides are not always entirely linear. For instance, polypeptides may be generally as a result of posttranslational events, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. Coli* or other cells, prior to proteolytic processing, almost invariably will be N-formylmethionine. During post-translational modification of the peptide, a methionine residue at the $NH_2$-terminus may be deleted. Accordingly, this invention contemplates the use of both the methionine-containing and the methionineless amino terminal variants of the protein of the invention. The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as, for example, *E. coli*. Accordingly, when glycosylation is desired, a polypeptide should be expressed in a glycosylating host, generally a eukaryotic cell. Insect cell often carry out the same posttranslational glycosylations as mammalian cells and, for this reason, insect cell expression systems have been developed to express efficiently mammalian proteins having native patterns of glycosylation, inter alia. Similar considerations apply to other modifications. It will be appreciated that the same type of modification may be present in the same or varying degree at several sites in a given polypeptide. Also, a given polypeptide may contain many types of modifications. In general, as used herein, the term polypeptide encompasses all such modifications, particularly those that are present in polypeptides synthesized recombinantly by expressing a polynucleotide in a host cell.

VARIANT(S) of polynucleotides or polypeptides, as the term is used herein, are polynucleotides or polypeptides that differ from a reference polynucleotide or polypeptide, respectively. Variants in this sense are described below and elsewhere in the present disclosure in greater detail. (1) A polynucleotide that differs in nucleotide sequence from another, reference polynucleotide. Generally, differences are limited so that the nucleotide sequences of the reference and the variant are closely similar overall and, in many regions, identical. As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below. (2) A polypeptide that differs in amino acid sequence from another, reference polypeptide. Generally, differences are limited so that the sequences of the reference and the variant are closely similar overall and, in many regions, identical. A variant and reference polypeptide may differ in amino acid sequence by one or more substitutions, additions, deletions, fusions and truncations, which may be present in any combination.

DETAILED DESCRIPTION OF THE INVENTION

The invention relates to a novel response regulator protein from *Staphylococcus aureus*, characterized in that it comprises the amino acid sequence given in SEQ ID NO: 2 or a fragment, analogue or derivative thereof. Hereinafter the term polypeptide(s) will be used to refer to the response regulator protein, its fragments, analogues or derivatives as well as the polypeptide fragment or its derivatives.

The invention relates especially to the gene having the nucleotide and amino acid sequences set out in FIG. 1 and FIG. 2 respectively, and to the nucleotide and amino acid sequences of the DNA of *S. aureus* WCUH 29 which has been deposited at the National Collection of Industrial and Marine Bacteria Ltd. (NCIMB), Aberdeen, Scotland under number NCIMB 40771 on Sep. 11, 1995. This is herein referred to as "the deposited DNA". It will be appreciated that the nucleotide and amino acid sequences set out in FIGS. 1 [SEQ ID NO:1] and 2 [SEQ ID NO:2] were obtained by sequencing the DNA of the deposit. Hence, the sequence of the deposit is controlling as to any discrepancies between it (and the sequence it encodes) and the sequences of FIGS. 1 [SEQ ID NO:1] and FIG. 2 [SEQ ID NO:2].

Techniques are available to evaluate temporal gene expression in bacteria, particularly as it applies to viability under laboratory and host infection conditions. A number of methods can be used to identify genes which are essential to survival per se, or essential to the establishment/ maintenance of an infection. Identification of expression of a sequence by one of these methods yields additional information about its function and permits the selection of such sequence for further development as a screening target. Briefly, these approaches include:

1) Signature Tagged Mutagenesis (STM)

This technique is described by Hensel et al., (1995) *Science* 269, 400–403, the content of which is incorporated by reference for background purposes. Signature tagged mutagenesis identifies genes necessary for the establishment/maintenance of infection in a given infection model.

The basis of the technique is the random mutagenesis of a target organism by various means (e.g., transposons) such that unique DNA sequence tags are inserted in close proximity to the site of mutation. The tags from a mixed population of bacterial mutants and bacteria recovered from infected hosts are detected by amplification, radiolabeling and hybridization analysis. Mutants attenuated in virulence are revealed by absence of the tag from the pool of bacteria recovered from infected hosts.

In *Streptococcus pneumoniae*, because the transposon system is less well developed, a more efficient way of creating the tagged mutants is to use the insertion-duplication mutagenesis technique as described by Morrison et al., (1984) *J. Bacteriol.* 159, 870, the content of which is incorporated by reference for background purposes.

2) In Vivo Expression Technology (IVET)

This technique is described by Camilli et al., (1994) *Proc. Nat'l. Acad. Sci. USA*. 91, 2634–2638, the content of which is incorporated by reference for background purposes. IVET identifies genes up-regulated during infection when compared to laboratory cultivation, implying an important role in infection. Sequences identified by this technique are implied to have a significant role in infection establishment/ maintenance.

In this technique random chromosomal fragments of target organism are cloned upstream of a promoter-less reporter gene in a plasmid vector. The pool is introduced into a host and at various times after infection bacteria may be recovered and assessed for the presence of reporter gene expression. The chromosomal fragment carried upstream of an expressed reporter gene should carry a promoter or portion of a gene normally upregulated during infection. Sequencing upstream of the reporter gene allows identification of the up regulated gene.

3) Differential display

This technique is described by Chuang et al., (1993) *J. Bacteriol.* 175, 2026–2036, the content of which is incorporated by reference for background purposes. This method identifies those genes which are expressed in an organism by identifying mRNA present using randomly-primed RT-PCR. By comparing pre-infection and post infection profiles, genes up and down regulated during infection can be identified and the RT-PCR product sequenced and matched to library sequences.

4) Generation of conditional lethal mutants by transposon mutagenesis.

This technique, described by de Lorenzo, V. et al., (1993) *Gene* 123, 17–24; Neuwald, A. F. et al., (1993) *Gene* 125, 69–73; and Takiff, H. E. et al., (1992) *J. Bacteriol.* 174, 1544–1553, the contents of which are incorporated by reference for background purposes, identifies genes whose expression are essential for cell viability.

In this technique transposons carrying controllable promoters, which provide transcription outward from the transposon in one or both directions, are generated. Random insertion of these transposons into target organisms and subsequent isolation of insertion mutants in the presence of inducer of promoter activity ensures that insertions which separate promoter from coding region of a gene whose expression is essential for cell viability will be recovered. Subsequent replica plating in the absence of inducer identifies such insertions, since they fail to survive. Sequencing of the flanking regions of the transposon allows identification of the site of insertion and identification of the gene disrupted. Close monitoring of the changes in cellular processes/morphology during growth in the absence of inducer yields information on likely function of the gene. Such monitoring could include flow cytometry (cell division, lysis, redox potential, DNA replication), incorporation of radiochemically labeled precursors into DNA, RNA, protein, lipid, peptidoglycan, monitoring reporter enzyme gene fusions which respond to known cellular stresses.

5) Generation of conditional lethal mutants by chemical mutagenesis.

This technique is described by Beckwith, J., (1991) *Methods in Enzymology* 204, 3–18, the content of which is incorporated herein by reference for background purposes. In this technique random chemical mutagenesis of target organism, growth at temperature other than physiological temperature (permissive temperature) and subsequent replica plating and growth at different temperature (e.g. 42° C. to identify ts, 25° C. to identify cs) are used to identify those isolates which now fail to grow (conditional mutants). As above, close monitoring of the changes upon growth at the non-permissive temperature yields information on the function of the mutated gene. Complementation of conditional lethal mutation by library from target organism and sequencing of complementing gene allows matching with library sequences.

Each of these techniques may have advantages or disadvantage depending on the particular application. The skilled artisan would choose the approach that is the most relevant with the particular end use in mind. For example, some genes might be recognized as essential for infection but in reality are only necessary for the initiation of infection and so their products would represent relatively unattractive targets for antibacterials developed to cure established and chronic infections.

6) RT-PCR

Bacterial messenger RNA, preferably that of Staphylococcus, is isolated from bacterial infected tissue, e.g., 48 hour murine lung infections, and the amount of each mRNA species assessed by reverse transcription of the RNA sample primed with random hexanucleotides followed by PCR with gene specific primer pairs. The determination of the presence and amount of a particular MRNA species by quantification of the resultant PCR product provides information on the bacterial genes which are transcribed in the infected tissue. Analysis of gene transcription can be carried out at different times of infection to gain a detailed knowledge of gene regulation in bacterial pathogenesis allowing for a clearer understanding of which gene products represent targets for screens for novel antibacterials. Because of the gene specific nature of the PCR primers employed, it should be understood that the bacterial mRNA preparation need not be free of mammalian RNA. This allows the investigator to carry out a simple and quick RNA preparation from infected tissue to obtain bacterial mRNA species which are very short lived in the bacterium (in the order of 2 minute half-lives). Optimally, the bacterial mRNA is prepared from infected murine lung tissue by mechanical disruption in the presence of TRIzole (GIBCO-BRL) for very short periods of time, subsequent processing according to the manufacturers of TRIzole reagent and DNAase treatment to remove contaminating DNA. Preferably the process is optimized by finding those conditions which give a maximum amount of bacterial 16S ribosomal RNA, preferably that of *Staphylococcius aureus*, as detected by probing Northerns with a suitably labeled sequence specific oligonucleotide probe. Typically, a 5' dye labelled primer is used in each PCR primer pair in a PCR reaction which is terminated optimally between 8 and 25 cycles. The PCR products are separated on 6% polyacrylamide gels with detection and quantification using GeneScanner (manufactured by ABI).

Use of the of these technologies when applied to the sequences of the present invention enables identification of bacterial proteins expressed during infection, inhibitors which would have utility in anti-bacterial therapy.

Polynucleotides

In accordance with one aspect of the present invention, there are provided isolated polynucleotides which encode the polypeptide having the deduced amino acid sequence of FIG. 2 [SEQ ID NO:2]. The term "polynucleotide encoding a polypeptide" as used herein encompasses polynucleotides which include a sequence encoding a polypeptide of the present invention, particularly bacterial, and more particularly the polypeptide of the invention having the amino acid sequence set out in FIG. 2 [SEQ ID NO:2]. The term encompasses polynucleotides that include a single continuous region or discontinuous regions encoding the polypeptide (for example, interrupted by integrated phage or insertion sequence or editing) together with additional regions, that also may contain coding and/or non-coding sequences.

Using the information provided herein, such as the polynucleotide sequence set out in FIG. 1 [SEQ ID NO:1], a polynucleotide of the present invention encoding SEQ ID NO:2 or a fragment thereof, may be obtained using standard cloning and screening procedures, such as those for cloning and sequencing chromosomal DNA fragments from *Staphylococcus aureus* cells as starting material, followed by obtaining a full length clone. For example, to obtain a polynucleotide of the invention sequence, such as that sequence given in FIG. 1 [SEQ ID NO:1], typically a library of clones of chromosomal DNA of *Staphylococcus aureus* in *E. coli* or some other suitable host is probed with a radio-labeled oligonucleotide, preferably a 17-mer or longer, derived from a partial sequence. Clones carrying DNA identical to that of the probe can then be distinguished using high stringency washes. By sequencing the individual clones thus identified with sequencing primers designed from the original sequence it is then possible to extend the sequence in both directions to determine the full gene sequence. Conveniently such sequencing is performed using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, N.Y. (1989). (See, Screening By Hybridization 1.90 and Sequencing Denatured Double-Stranded DNA Templates 13.70). Illustrative of the invention, the polynucleotide set out in FIG. 1 [SEQ ID NO:1] was discovered in a DNA library derived from *Staphylococcus aureus*.

The gene of the invention [SEQ ID NO:1] is structurally related to other response regulators, as shown by the results of sequencing of the gene characterized by the DNA of the deposited *S. aureus* WCUH 29. The DNA sequence thus obtained is set out in FIG. 1 [SEQ ID NO:1]. It contains an open reading frame encoding a protein of having about the number of amino acid residues set forth in FIG. 2 [SEQ ID NO:2] with a deduced molecular weight that can be calculated using amino acid residue molecular weight values well known in the art. The polypeptide of FIG. 2 [SEQ ID NO:2] has about 37% identity to the PhoP regulatory protein from *Bacillus subtilis*.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

The sequence which encodes the polypeptide may be identical to the coding sequence of the polynucleotide shown in FIG. 1 [SEQ ID NO:1]. It also may be a polynucleotide with a different sequence, which, as a result of the redundancy (degeneracy) of the genetic code, encodes the polypeptide of FIG. 2 [SEQ ID NO:2].

Polynucleotides of the present invention which encode the polypeptide of FIG. 2 [SEQ ID NO:2] may include, but are not limited to the coding sequence for the mature polypeptide, by itself; the coding sequence for the mature polypeptide and additional coding sequences, such as those encoding a leader or secretory sequence, such as a pre-, or pro- or prepro- protein sequence; the coding sequence of the mature polypeptide, with or without the aforementioned additional coding sequences, together with additional, non-coding sequences, including for example, but not limited to non-coding 5' and 3' sequences, such as the transcribed, non-translated sequences that play a role in transcription (including termination signals, for example), ribosome binding, mRNA stability elements, and additional coding sequence which encode additional amino acids, such as those which provide additional functionalities. Thus, for instance, the polypeptide may be fused to a marker sequence, such as a peptide, which facilitates purification of the fused polypeptide. In certain embodiments of this aspect of the invention, the marker sequence is a hexa-histidine peptide, such as the tag provided in the pQE vector (Qiagen, Inc.), among others, many of which are commercially available. As described in Gentz et al., (1989) *Proc. Natl. Acad. Sci. USA* 86, 821–824, for instance, hexa-histidine provides for convenient purification of the fusion protein. The HA tag may also be used to create fusion proteins and corresponds to an epitope derived of influenza hemagglutinin protein, which has been described by Wilson et al., (1984) *Cell* 37, 767, for instance. Polynucleotides of the invention also include, but are not limited to, polynucleotides comprising a structural gene and its naturally associated genetic elements.

The present invention further relates to variants of the herein above described polynucleotides which encode fragments, analogs and derivatives of the polypeptide having the deduced amino acid sequence of FIG. 2 [SEQ ID NO:2]. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence set out in FIG. 2 [SEQ ID NO:2]; variants, analogs, derivatives and fragments thereof, and fragments of the variants, analogs and derivatives.

Further particularly preferred in this regard are polynucleotides encoding variants, analogs, derivatives and fragments of SEQ ID NO:1, and variants, analogs and derivatives of the fragments, which have the amino acid sequence of the polypeptide of FIG. 2 [SEQ ID NO:2] in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the gene of SEQ ID NO:1. Also especially preferred in this regard are conservative substitutions. Most highly preferred are polynucleotides encoding polypeptides having the amino acid sequence of FIG. 2 [SEQ ID NO:2], without substitutions.

Further preferred embodiments of the invention are polynucleotides that are at least 70% identical over their entire length to a polynucleotide encoding the polypeptide having the amino acid sequence set out in FIG. 2 [SEQ ID NO:2], and polynucleotides which are complementary to such polynucleotides. Alternatively, most highly preferred are polynucleotides that comprise a region that is at least 80% identical over their entire length to a polynucleotide encoding the polypeptide of the DNA of the deposited *S. aureus* WCUH 29 and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred. The polynucleotides which hybridize to the hereinabove described polynucleotides in a preferred embodiment encode polypeptides which retain substantially the same biological function or activity as the polypeptide characterized by the deduced amino acid sequence of SEQ ID NO: 2.

Preferred embodiments in this respect, moreover, are polynucleotides which encode polypeptides which retain substantially the same biological function or activity as the mature polypeptide encoded by the DNA of FIG. 1 [SEQ ID NO:1]. The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention as discussed above, may be used as a hybridization probe for RNA, cDNA and genomic DNA to isolate full-length cDNAs and genomic clones encoding the sequences of SEQ ID NO:1 and to isolate cDNA and genomic clones of other genes that have a high sequence similarity to SEQ ID NO:1. Such probes generally will comprise at least 15 bases. Preferably, such probes will have at least 30 bases and may have at least 50 bases. Particularly preferred probes will have at least 30 bases and will have 50 bases or less. For example, the coding region of the gene of the invention may be isolated by screening using the known DNA sequence to synthesize an oligonucleotide probe. A labeled oligonucleotide having a sequence complementary to that of a gene of the present invention is then used to screen a library of cDNA, genomic DNA or mRNA to determine to which members of the library the probe hybridizes.

The polynucleotides and polypeptides of the present invention may be employed as research reagents and materials for discovery of treatments of and diagnostics for disease, particularly human disease, as further discussed herein relating to polynucleotide assays, inter alia.

The polynucleotides of the invention that are oligonucleotides, derived from the sequences of SEQ ID NO:1 may be used in the processes herein as described, but preferably for PCR, to determine whether or not the gene identified herein in whole or in part are transcribed in infected tissue. It is recognized that such sequences will also have utility in diagnosis of the stage of infection and type of infection the pathogen has attained.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Deposited materials

The deposit has been made under the terms of the Budapest Treaty on the International Recognition of the Deposit of Micro-organisms for Purposes of Patent Procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. §112. S. aureus WCUH 29 has been deposited at the National Collections of Industrial and Marine Bacteria Ltd. (NCIMB), 23 St. Machar Drive, Aberdeen AB2 1RY Aberdeen, Scotland under number NCIMB 40771 on Sep. 11, 1995. The sequence of the polynucleotides contained in the deposited material, as well as the amino acid sequence of the polypeptide encoded thereby, are controlling in the event of any conflict with any description of sequences herein.

A license may be required to make, use or sell the deposited materials. No such license is hereby granted.

Polypeptides

The present invention further relates to a novel *Staphylococcus aureus* response regulator protein which has a deduced amino acid sequence of 233 amino acids in length, as set forth in FIG. 2 [SEQ ID NO:2]. The polypeptide of the present invention may be a recombinant polypeptide, a natural polypeptide or a synthetic polypeptide, preferably a recombinant polypeptide.

The invention also relates to fragments, analogs and derivatives of these polypeptides. The terms "fragment," "derivative" and "analog" when referring to the polypeptide of FIG. 2 [SEQ ID NO:2], means a polypeptide which retains essentially the same biological function or activity as such polypeptide. Thus, an analog includes a proprotein which can be activated by cleavage of the proprotein portion to produce an active mature polypeptide.

The fragment, derivative or analog of the polypeptide of FIG. 2 [SEQ ID NO:2] may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among the particularly preferred embodiments of the invention in this regard are polypeptides having the amino acid sequence of the novel response regulator protein set out in FIG. 2 [SEQ ID NO:2], variants, analogs, derivatives and fragments thereof, and variants, analogs and derivatives of the fragments. Alternatively, particularly preferred embodiments of the invention in this regard are polypeptides having the amino acid sequence of SEQ ID NO:2, variants, analogs, derivatives and fragments thereof, and variants, analogs and derivatives of the fragments.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Further particularly preferred in this regard are variants, analogs, derivatives and fragments, and variants, analogs and derivatives of the fragments, having the amino acid sequence of the polypeptide of FIG. 2 [SEQ ID NO:2], in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the polypeptide of the invention. Also especially preferred in this regard are conservative substitutions. Most highly preferred are polypeptides having the amino acid sequence of FIG. 2 [SEQ ID NO:2] without substitutions. Preferably, the fragment, derivative or analogue of the polypeptide characterized by the deduced amino acid sequence of SEQ ID NO: 2, retains essentially the same biological function or activity as such polypeptide. Thus, an analogue includes a proprotein which can be activated by cleavage of the proprotein portion to produce an active mature polypeptide.

The polypeptides and polynucleotides of the present invention are preferably provided in an isolated form, and preferably are purified to homogeneity.

The polypeptides of the present invention include the polypeptide of FIG. 2 [SEQ ID NO:2] (in particular the mature polypeptide) as well as polypeptides which have at least 70% identity to the polypeptide of FIG. 2 [SEQ ID NO:2], preferably at least 80% identity to the polypeptide of FIG. 2 [SEQ ID NO:2], and more preferably at least 90% similarity (more preferably at least 90% identity) to the polypeptide of FIG. 2 [SEQ ID NO:2] and still more preferably at least 95% similarity (still more preferably at least 95% identity) to the polypeptide of FIG. 2 [SEQ ID NO:2] and also include portions of such polypeptides with such portion of the polypeptide generally containing at least 30 amino acids and more preferably at least 50 amino acids.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

Fragments

Also among preferred embodiments of this aspect of the present invention are polypeptides comprising fragments of SEQ ID NO:2 (FIG. 2), and fragments of variants and derivatives of the polypeptide of FIG. 2 [SEQ ID NO:2].

In this regard a fragment is a polypeptide having an amino acid sequence that entirely is the same as part but not all of the amino acid sequence of the aforementioned polypeptides and variants or derivatives thereof.

Such fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a polypeptide of the invention comprised within a precursor polypeptide designed for expression in a host and having heterologous pre- and pro-polypeptide regions fused to the amino terminus of the fragment and an additional region fused to the carboxyl terminus of the fragment. Therefore, fragments in one aspect of the meaning intended herein, refers to the portion or portions of a fusion polypeptide or fusion protein derived from SEQ ID NO:2.

Representative examples of polypeptide fragments of the invention, include, for example, fragments from amino acid number about1 to about 20, about 21 to about 40, about 41 to about 60, about 61 to about 80, about 81 to about 100, and about 101 to about 224, and any combination of these 20 amino acid fragments. In this context "about" includes the particularly recited ranges larger or smaller by several, a few, 5, 4, 3, 2 or1 amino acid at either extreme or at both extremes.

Preferred fragments of the invention include, for example, truncation polypeptides of SEQ ID NO:2. Truncation polypeptides include polypeptides having the amino acid sequence of FIG. 2, or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out above also are preferred embodiments of truncation fragments, which are especially preferred among fragments generally. Degradation forms of the polypeptides of the invention in a host cell, particularly a Staphylococcus, are also preferred.

Also preferred in this aspect of the invention are fragments characterized by structural or functional attributes of the polypeptide characterized by the sequences of SEQ ID NO:2. Preferred embodiments of the invention in this regard include fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, high antigenic index regions of the polypeptide of the invention, and combinations of such fragments. Preferred regions are those that mediate activities of the polypeptides of the invention. Most highly preferred in this regard are fragments that have a chemical, biological or other activity of the response regulator polypeptide of the invention, including those with a similar activity or an improved activity, or with a decreased undesirable activity. Further preferred polypeptide fragments are those that are antigenic or immunogenic in an animal, especially in a human.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspond to the preferred fragments, as discussed above.

Vectors, host cells, expression

The present invention also relates to vectors which comprise a polynucleotide or polynucleotides of the present invention, host cells which are genetically engineered with vectors of the invention and the production of polypeptides of the invention by recombinant techniques.

Host cells (as defined herein) can be genetically engineered to incorporate polynucleotides of the invention and express polypeptides of the present invention. Introduction of a polynucleotide into the host cell can be affected by calcium phosphate transfection, DEAE-dextran mediated transfection, transvection, microinjection, cationic lipid-mediated transfection, electroporation, transduction, scrape loading, ballistic introduction, infection or other methods. Such methods are described in many standard laboratory manuals, such as Davis et al., BASIC METHODS IN MOLECULAR BIOLOGY, (1986) and Sambrook et al., MOLECULAR CLONING: A LABORATORY MANUAL, 2nd Ed., Cold Spring Harbor Laboratory Press, Cold Spring Harbor, N.Y. (1989). The engineered host cells can be cultured in conventional nutrient media modified as appropriate for activating promoters, selecting transformants or amplifying the genes. The culture conditions, such as temperature, pH and the like, are those previously used with the host cell selected for expression, and will be apparent to the ordinarily skilled artisan.

Polynucleotide constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *MOLECULAR CLONING: A LABORATORY MANUAL*, 2nd Ed., Cold Spring Harbor Laboratory Press, Cold Spring Harbor, N.Y. (1989).

In accordance with this aspect of the invention the vector may be, for example, a plasmid vector, a single or double-stranded phage vector, a single or double-stranded RNA or DNA viral vector. Plasmids generally are designated herein by a lower case p preceded and/or followed by capital letters and/or numbers, in accordance with standard naming conventions that are familiar to those of skill in the art. Starting plasmids disclosed herein are either commercially available, publicly available, or can be constructed from available plasmids by routine application of well known, published procedures. Many plasmids and other cloning and expression vectors that can be used in accordance with the present invention are well known and readily available to those of skill in the art.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

A great variety of expression vectors can be used to express a polypeptide of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard. Selection of the appropriate vector is well within the level of ordinary skill in the art.

The appropriate DNA sequences of the invention may be inserted into the vector in a forward or reverse orientation by any of a variety of well-known and routine techniques, such as, for example, those set forth in Sambrook et al., *MOLECULAR CLONING, A LABORATORY MANUAL*, 2nd Ed.; Cold Spring Harbor Laboratory Press, Cold Spring Harbor, N.Y. (1989).

The DNA sequence in the expression vector is operatively linked to appropriate expression control sequence(s), including, for instance, a promoter to direct mRNA transcription, a ribosome binding site (for bacterial expression) and, optionally, an operator (collectively referred to herein as "control elements"), to permit expression. Representatives of such promoters include, but are not limited to, the phage lambda PL promoter, the *E. coli* lac, trp and tac promoters, the SV40 early and late promoters and promoters of retroviral LTRs, the protein A gene (spa) promoter and signal sequence, and other promoters known to control expression of genes in eukaryotic or prokaryotic cells or their viruses.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition to control sequences, it may be desirable to add regulatory sequences which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences. Generally, in accordance with many commonly practiced procedures, such regions will operate by regulating transcription, such as transcription factors, repressor binding sites and termination, among others. Vectors for propagation and expression generally will include selectable markers and amplification regions, such as, for example, those set forth in Sambrook et al., cited above.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the coding sequences may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site. The coding sequence may contain a signal peptide or leader sequence. Leader sequences can be removed by the bacterial host in post-translational processing. See, e.g., U.S. Pat. Nos. 4,431,739; 4,425,437; 4,338,397.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Representative examples of appropriate hosts include bacterial cells, such as streptococci, staphylococci, E. coli, streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

The following vectors, which are commercially available, are provided by way of example. Among vectors preferred for use in bacteria are pQE70, pQE60 and pQE-9, available from Qiagen; pET-3 vectors (Stratagene), pD10, psiX174, pbsks, pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia, and pBR322 (ATCC 37017). Among preferred eukaryotic vectors are pWLNEO, pSV2CAT, pOG44, pXT1 and pSG available from Stratagene; and pSVK3, pBPV, pMSG and pSVL available from Pharmacia. Examples of recombinant DNA vectors for cloning and host cells which they can transform include the bacteriophage (E. coli), pBR322 (E. coli), pACYC 177 (E. coli), pKT230 (gram-negative bacteria), pGV1106 (gram-negative bacteria), pLAFR1 (gram-negative bacteria), pME290 (non-E. coli gram-negative bacteria), pHV14 (E. coli and Bacillus subtilis), pBD9 (Bacillus), pIJ61 (Streptomyces), pUC6 (Streptomyces), YIp5 (Saccharomyces), a baculovirus insect cell system, YCp19 (Saccharomyces). See, generally, "DNA Cloning": Vols. I & II, Glover et al. ed. IRL Press Oxford (1985) (1987) and; T. Maniatis et al. ("Molecular Cloning" Cold Spring Harbor Laboratory (1982). These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available, such as pKK232-8 and pCM7. Promoters for expression of polynucleotides of the present invention include not only well known and readily available promoters, but also promoters that readily may be obtained by the foregoing technique, using a reporter gene.

Among known prokaryotic promoters suitable for expression of polynucleotides and polypeptides in accordance with the present invention are the E. coli lacI and lacZ promoters, the T3 and T7 promoters, the gpt promoter, the lambda PR, PL promoters and the trp promoter.

Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Recombinant expression vectors will include, for example, origins of replication, a promoter preferably derived from a highly-expressed gene to direct transcription of a downstream structural sequence, and one or more selectable markers to permit isolation of vector containing cells after exposure to the vector. For example, a selectable marker may provide a phenotypic trait for selection of transformed host cells such as dihydrofolate reductase or neomycin resistance for eukaryotic cell culture, or such as tetracycline or ampicillin resistance in E. coli.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiation codon. Also, generally, there will be a translation stop codon at the end of the polypeptide and there will be a polyadenylation signal in constructs for use in eukaryotic hosts. Transcription termination signal appropriately disposed at the 3' end of the transcribed region may also be included in the polynucleotide construct.

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N- or C-terminus of the polypeptide to improve stability and persistence in the host cell, during purification or during subsequent handling and storage. Also, a region may be added to the polypeptide to facilitate purification. Such a region may be removed prior to final preparation of the polypeptide. The addition of peptide moieties to polypeptides to engender secretion or excretion, to improve stability or to facilitate purification, among others, are familiar and routine techniques in the art. A preferred fusion protein comprises a heterologous region from an immunoglobulin that is useful to solubilize or purify polypeptides. For example, EP-A-O 464 533 (Canadian counterpart 2045869) discloses fusion proteins comprising various portions of constant region of immunoglobulin molecules together with another protein or part thereof. In drug discovery, for example, proteins have been fused with antibody Fc portions for the purpose of high-throughput screening assays to identify antagonists. See, D. Bennett et al., (1995) *Journal of Molecular Recognition*, 8, 52–58 and K. Johanson et al., (1995) *The Journal of Biological Chemistry*, 270(16), 9459–9471.

Depending on the expression system and host selected, the polypeptide of the present invention may be produced by growing host cells transformed by an expression vector described above under conditions whereby the polypeptide of interest is expressed. Where the mature protein has a very hydrophobic region which leads to an insoluble product of overexpression, it may be desirable to express a truncated protein in which the hydrophobic region has been deleted. The selection of the appropriate growth conditions and recovery methods are within the skill of the art.

Depending upon the host employed in a recombinant production procedure, the polypeptides of the present invention may be glycosylated or may be non-glycosylated. Polypeptides of the invention may also include an initial methionine amino acid residue. The polypeptide is then isolated from the host cells and purified. If the expression system secretes the polypeptide into growth media, the polypeptide can be purified directly from the media. If the polypeptide is not secreted, it is isolated from cell lysates or recovered from the cell membrane fraction. Where the polypeptide is localized to the cell surface, whole cells or isolated membranes can be used as an assayable source of the desired gene product.

Cells typically then are harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, such methods are well know to those skilled in the art.

A polypeptide of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding protein may be employed to regenerate active conformation when the polypeptide is denatured during isolation and or purification.

Polynucleotide assays

This invention is also related to the use of the polynucleotides of the invention to detect complementary polynucleotides such as, for example, as a diagnostic reagent. Detection of a gene characterized by the sequences of SEQ ID NO:1 in a eukaryote, particularly a mammal, and especially a human, will provide a diagnostic method for diagnosis of a disease. Eukaryotes (herein also "individual(s)"), particularly mammals, and especially humans, infected with an organism comprising the gene of the invention may be detected at the DNA level by a variety of techniques. Nucleic acids for diagnosis may be obtained from an infected individual's cells and tissues, such as bone, blood, muscle, cartilage, and skin. Genomic DNA may be used directly for detection or may be amplified enzymatically by using PCR (Saiki et al., (1986) *Nature*, 324, 163–166) prior to analysis. RNA or cDNA may also be used in the same ways. As an example, PCR primers complementary to the nucleic acid of SEQ ID NO:1 can be used to identify and analyze presence and/or expression of the gene. Using PCR, characterization of the strain of prokaryote present in a eukaryote, particularly a mammal, and especially a human, may be made by an analysis of the genotype of the prokaryote gene. For example, deletions and insertions can be detected by a change in size of the amplified product in comparison to the genotype of a reference sequence. Point mutations can be identified by hybridizing amplified DNA to radiolabeled RNA or alternatively, radiolabeled antisense DNA sequences. Perfectly matched sequences can be distinguished from mismatched duplexes by RNaseA digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic characterization based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., (1985) *Science*, 230, 1242).

Sequence changes at specific locations also may be revealed by nuclease protection assays, such as RNase and S1 protection or the chemical cleavage method (e.g., Cotton et al., (1985) *Proc. Natl. Acad. Sci. USA*, 85, 4397–4401).

Thus, the detection of a specific DNA sequence may be achieved by methods such as hybridization, RNase protection, chemical cleavage, direct DNA sequencing or the use of restriction enzymes, e.g., restriction fragment length polymorphisms (RFLP) and Southern blotting of genomic DNA.

In addition to more conventional gel-electrophoresis and DNA sequencing, mutations also can be detected by in situ analysis.

Cells carrying mutations or polymorphisms in the gene of the present invention may also be detected at the DNA level by a variety of techniques, to allow for serotyping, for example. For example, RT-PCR can be used to detect mutations. It is particularly preferred to used RT-PCR in conjunction with automated detection systems, such as, for example, GeneScan. RNA or cDNA may also be used for the same purpose, PCR or RT-PCR. As an example, PCR primers complementary to the nucleic acid encoding SEQ ID NO:2 can be used to identify and analyze mutations. Suitable primers may include fragments of SEQ ID NO:1, preferably of at least 15 base pairs in length, as well as sequences complementary thereto. The primers may be used to amplify the gene isolated from the individual such that the gene may then be subject to various techniques for elucidation of the DNA sequence. In this way, mutations in the DNA sequence may be diagnosed.

The invention provides a process for diagnosing disease, preferably bacterial infections, more preferably Staphylococcus, comprising determining from a sample derived from an individual a increased level of expression of polynucleotide having the sequence of FIG. 1 [SEQ ID NO: 1]. Increased expression of the polynucleotide of the invention can be measured using any one of the methods well known in the art for the quantitation of polynucleotides, such as, for example, PCR, RT-PCR, RNase protection, Northern blotting and other hybridization methods.

Polypeptide assays

The present invention also relates to diagnostic assays such as quantitative and diagnostic assays for detecting levels of the proteins and polypeptides of the invention in cells and tissues, including determination of normal and abnormal levels. Thus, for instance, a diagnostic assay in accordance with the invention for detecting over-expression of a protein of the invention compared to normal control tissue samples may be used to detect the presence of an infection, for example. Assay techniques that can be used to determine levels of a protein of the invention, in a sample derived from a host are well-known to those of skill in the art. Such assay methods include radioimmunoassays, competitive-binding assays, Western Blot analysis and ELISA assays. Among these ELISAs frequently are preferred. An ELISA assay initially comprises preparing an antibody specific to a polypeptide of the invention, particularly a polypeptide characterized by the amino acid sequence of SEQ ID NO:2 or a derivative thereof. Preferably the antibody is a monoclonal antibody. In addition, a reporter antibody generally is prepared which binds to the monoclonal antibody. The reporter antibody is attached to a detectable reagent such as radioactive, fluorescent or enzymatic reagent, for example, horseradish peroxidase enzyme.

Antibodies

The polypeptides, their fragments or other derivatives, or analogs thereof, or cells expressing them can be used as an immunogen to produce antibodies thereto. The present invention includes, for examples monoclonal and polyclonal antibodies, chimeric, single chain, and humanized antibodies, as well as Fab fragments, or the product of an Fab expression library.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique known in the art which provides antibodies produced by continuous cell line cultures can be used. Examples include various techniques, such as those in Kohler, G. and Milstein, C., (1975) Nature 256, 495–497; Kozbor et at., (1983) Immunology Today 4: 72; Cole et al., pg. 77–96 in MONOCLONAL ANTIBODIES AND CANCER THERAPY, Alan R. Liss, Inc. (1985).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

Alternatively phage display technology could be utilized to select antibody genes with binding activities towards the polypeptide either from repertoires of PCR amplified v-genes of lymphocytes from humans screened for possessing anti-Fbp or from naive libraries (McCafferty, J. et al., (1990), Nature, 348, 552–554; Marks, J. et al., (1992) Biotechnology, 10, 779–783). The affinity of these antibodies can also be improved by chain shuffling (Clackson, T. et al., (1991) Nature, 352, 624–628).

If two antigen binding domains are present each domain may be directed against a different epitope—termed 'bispecific' antibodies.

The above-described antibodies may be employed to isolate or to identify clones expressing the polypeptide or purify the polypeptide of the present invention by attachment of the antibody to a solid support for isolation and/or purification by affinity chromatography.

Thus, among others, antibodies against the polypeptides of the invention may be employed to inhibit and/or treat infections, particularly bacterial infections and especially Staphylococcal infections.

Polypeptide derivatives include antigenically, epitopically or immunologically equivalent derivatives which form a particular aspect of this invention. The term "antigenically equivalent derivative" as used herein encompasses a polypeptide or its equivalent which will be specifically recognized by certain antibodies which, when raised to the protein or polypeptide according to the present invention, interfere with the immediate physical interaction between pathogen and mammalian host. The term "immunologically equivalent derivative" as used herein encompasses a peptide or its equivalent which when used in a suitable formulation to raise antibodies in a vertebrate, the antibodies act to interfere with the immediate physical interaction between pathogen and mammalian host.

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively, a multiple antigenic peptide comprising multiple copies of the protein or polypeptide, or an antigenically or immunologically equivalent polypeptide thereof may be sufficiently antigenic to improve immunogenicity so as to obviate the use of a carrier.

Preferably the antibody or derivative thereof is modified to make it less immunogenic in the individual. For example, if the individual is human the antibody may most preferably be "humanized"; where the complimentarity determining region(s) of the hybridomaderived antibody has been transplanted into a human monoclonal antibody, for example as described in Jones, P. et al., (1986), Nature 321, 522–525 or Tempest et al., (1991) Biotechnology 9, 266–273.

The use of a polynucleotide of the invention in genetic immunization will preferably employ a suitable delivery method such as direct injection of plasmid DNA into muscles (Wolff et al., (1992) Hum Mol Genet, 1:363, Manthorpe et al., (1963) Hum. Gene Ther., 4, 419), delivery of DNA complexed with specific protein carriers (Wu et al., (1989) J Biol Chem, 264, 16985), coprecipitation of DNA with calcium phosphate (Benvenisty & Reshef, (1986) Proc. Natl. Acad. Sci., 83, 9551), encapsulation of DNA in various forms of liposomes (Kaneda et al., (1989) Science 243, 375), particle bombardment (Tang et al., (1992) Nature 356, 152, Eisenbraun et al., (1993) DNA Cell Biol, 12, 791) and in vivo infection using cloned retroviral vectors (Seeger et al., (1984) Proc. Natl. Acad. Sci. USA, 81, 5849).

Binding Molecules and Assays

This invention also provides a method for identification of molecules, such as binding molecules, that bind the polynucleotides and polypeptides of the invention. Genes encoding such binding proteins can be identified by numerous methods known to those of skill in the art, for example, ligand panning and FACS sorting. Such methods are described in many laboratory manuals such as, for instance, Coligan et al., Current Protocols in Immunology 1(2): Chapter 5 (1991). Also, a labeled ligand can be photoaffinity linked to a cell extract.

Polypeptides of the invention also can be used to assess the binding capacity of these molecules in cells or in cell-free preparations.

Polypeptides of the invention may also be used to assess the binding or small molecule substrates and ligands in, for example, cells, cell-free preparations, chemical libraries, and natural product mixtures. These substrates and ligands may be natural substrates and ligands or may be structural or functional mimetics.

Antagonists and agonists—assays and molecules

The invention also provides a method of screening compounds to identify those which enhance (agonist) or block (antagonist) the action of the polypeptides or polynucleotides of the invention, such as their interaction with the binding molecules of the invention.

For example, to screen for agonists or antagonists, a synthetic reaction mix, a cellular compartment, such as a membrane, cell envelope or cell wall, or a preparation of any thereof, may be prepared from a cell that expresses a molecule that binds a polynucleotide or polypeptide of the invention. The preparation is incubated with a labeled polypeptide or polynucleotide of the invention in the absence or the presence of a candidate molecule which may be an agonist or antagonist. The ability of the candidate molecule to bind the binding molecule is reflected in decreased binding of the labeled ligand. Molecules which bind gratuitously are most likely to be good antagonists. Molecules that bind well and elicit effects that are the same as or closely related to the polynucleotides or polypeptides of the invention are agonists.

The effects, e.g., anti-bacterial effects, of potential agonists and antagonists may be measured, for instance, by determining activity of a reporter system following interaction of the candidate molecule with a cell or appropriate cell preparation, and comparing the effect with that of the polynucleotides and polypeptides of the invention or molecules that elicit the same effects as the compositions of the invention. Reporter systems that may be useful in this regard include but are not limited to colorimetric labeled substrate converted into product, a reporter gene that is responsive to changes in activity, and binding assays known in the art.

Another example of an assay for antagonists is a competitive assay that combines a polypeptide or polynucleotide of the invention and a potential antagonist with membrane-bound molecules which bind the polynucleotides or polypeptides of the invention, recombinant binding molecules, natural substrates or ligands, or substrate or ligand mimetics, under appropriate conditions for a competitive inhibition assay. The polynucleotides and polypeptides of the invention can be labeled, such as by radioactivity or a calorimetric compound, such that the number of molecules of the invention bound to a binding molecule or converted to product can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a binding molecule, without inducing activity of the polypeptide or polynucleotide of the invention, thereby preventing the action of the molecule by excluding the molecule from binding.

Potential antagonists include a small molecule which binds to and occupies the binding site of the polypeptide thereby preventing binding to cellular binding molecules, such that normal biological activity is prevented. Examples of small molecules include but are not limited to small organic molecules, peptides or peptide-like molecules.

Other potential antagonists include antisense molecules (see Okano, (1991) *J. Neurochem.*, 56,560; *OLIGODEOXY-NUCLEOTIDES AS ANTISENSE INHIBITORS OF GENE EXPRESSION*, CRC Press, Boca Raton, Fla. (1988), for a description of these molecules).

Preferred potential antagonists include compounds related to and derivatives of the gene of the invention.

In a particular aspect the invention provides the use of the polypeptide, polynucleotide or inhibitor of the invention to interfere with the initial physical interaction between a pathogen and mammalian host responsible for sequelae of infection. In particular the molecules of the invention may be used: i) in the prevention of adhesion of bacteria, in particular gram positive bacteria, to mammalian extracellular matrix proteins on in-dwelling devices or to extracellular matrix proteins in wounds; ii) to block response regulator protein mediated mammalian cell invasion by, for example, initiating phosphorylation of mammalian tyrosine kinases (Rosenshine et al., (1992) *Infect. Immun.*, 60, 221 1; iii) to block bacterial adhesion between mammalian extracellular matrix proteins and bacterial response regulator proteins which mediate tissue damage; iv) to block the normal progression of pathogenesis in infections initiated other than by the implantation of in-dwelling devices or by other surgical techniques.

Each of the DNA sequences provided herein may be used in the discovery and development of antibacterial compounds. The encoded protein upon expression can be used as a target for the screening of antibacterial drugs. Additionally, the DNA sequences encoding the amino terminal regions of the encoded protein or Shine-Delgarno or other translation facilitating sequences of the respective mRNA can be used to construct antisense sequences to control the expression of the coding sequence of interest.

The antagonists and agonists may be employed for instance to inhibit bacterial infections, particularly Staphylococcal infections.

In a further aspect, this invention provides a method of screening drugs to identify those which i) interfere with the interaction of the response regulator with a histidine kinase, the method comprising incubating the response regulator with histidine kinase in the presence of the drug and measuring the ability of the drug to block this interaction; ii) interfere with the ability of the response regulator to catalyze the transfer of phosphate group from the histidine kinase to itself, the method comprising incubating the response regulator with drug and measuring the ability of the response regulator to catalyze the removal of phosphate from phosphorylated histidine kinase; and/or iii) interfere with the ability of the molecule to autodephosphorylate itself once the phosphate had been transferred, the method comprising incubating the phosphorylated response regulator with drug and measuring the ability of the response regulator to catalyze the autodephosphorylation.

The histidine kinase is preferably the cognate histidine kinase of the response regulator, or another histidine kinase which is capable of acting as a substrate for the response regulator, and is preferably from *Staph. aureus* but may be from another microorganism, e.g., Bacillus. Generally the genes for a histidine kinase and its cognate response regulator are found close together on the chromosome so a suitable histidine kinase may conveniently be identified by further sequencing along the chromosome.

The invention also relates to inhibitors identified thereby.

Vaccines

Another aspect of the invention relates to a method for inducing an immunological response in an individual, particularly a mammal which comprises inoculating the individual with the gene of the invention, or a fragment or variant thereof, adequate to produce antibody to protect said individual from infection, particularly bacterial infection and most particularly Staphylococcal infections. Yet another aspect of the invention relates to a method of inducing immunological response in an individual which comprises, through gene therapy, delivering gene characterized by the sequences of SEQ ID NOs: 1 and 2, or a fragment or a variant thereof, for expressing the gene, or a fragment or a variant thereof in vivo in order to induce an immunological response to produce antibody to protect said individual from disease.

A further aspect of the invention relates to an immunological composition which, when introduced into a host capable or having induced within it an immunological response, induces an immunological response in such host to a gene characterized by the polynucleotide sequences of the invention or protein coded therefrom, wherein the composition comprises a recombinant gene or protein coded therefrom comprising DNA which codes for and expresses an antigen of said gene or protein coded therefrom.

The gene or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as Glutathione-S-transferase (GST) or beta-galactosidase, relatively large co-proteins which solubilize the protein and facilitate production and purification thereof. Moreover, the co-protein may act as an adjuvant in the sense of providing a generalized stimulation of the immune system. The co-protein may be attached to either the amino or carboxy terminus of the first protein.

Provided by this invention are compositions, particularly vaccine compositions, and methods comprising the polypeptides or polynucleotides of the invention and immunostimulatory DNA sequences, such as those described in Sato, Y. et al., (1996) *Science*, 273, 352.

Also, provided by this invention are methods using the described polynucleotide or particular fragments thereof which have been shown to encode non-variable regions of bacterial cell surface proteins in DNA constructs used in such genetic immunization experiments in animal models of infection with Staphylococcus will be particularly useful for identifying protein epitopes able to provoke a prophylactic or therapeutic immune response. It is believed that this approach will allow for the subsequent preparation of monoclonal antibodies of particular value from the requisite organ of the animal successfully resisting or clearing infection for the development of prophylactic agents or therapeutic treatments of Staphylococcal infection in mammals, particularly humans.

The polypeptide may be used as an antigen for vaccination of a host to produce specific antibodies which protect against invasion of bacteria, for example by blocking adherence of bacteria to damaged tissue. Examples of tissue damage include wounds in skin or connective tissue caused, e.g., by mechanical, chemical or thermal damage or by implantation of in-dwelling devices, or wounds in the mucous membranes, such as the mouth, mammary glands, urethra or vagina.

The present invention also includes a vaccine formulation which comprises the immunogenic recombinant protein together with a suitable carrier. Since the protein may be broken down in the stomach, it is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostatics and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to the gene characterized by the polynucleotide sequences of SEQ ID NO: 1 and the amino acid sequences of SEQ ID NO: 2, it is to be understood that this covers fragments of the naturally occurring protein and similar proteins with additions, deletions or substitutions which do not substantially affect the immunogenic properties of the recombinant protein.

Compositions

The invention also relates to compositions comprising the polynucleotide or the polypeptides discussed above or the agonists or antagonists. Thus, the polypeptides of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

Kits

The invention further relates to diagnostic and pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Administration

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of at least about 10 µg/kg body weight. In most cases they will be administered in an amount not in excess of about 8 mg/kg body weight per day. Preferably, in most cases, dose is from about 10 μg/kg to about1 mg/kg body weight, daily. It will be appreciated that optimum dosage will be determined by standard methods for each treatment modality and indication, taking into account the indication, its severity, route of administration, complicating conditions and the like.

In therapy or as a prophylactic, the active agent may be administered to an individual as an injectable composition, for example as a sterile aqueous dispersion, preferably isotonic.

Alternatively, the composition may be formulated for topical application, for example, in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters, etc.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent Staphylococcal wound infections.

Many orthopaedic surgeons consider that humans with prosthetic joints should be considered for antibiotic prophylaxis before dental treatment that could produce a bacteremia. Late deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis. Alternatively, the composition of the invention may be used to bathe an in-dwelling device immediately before insertion. The active agent will preferably be present at a concentration of1 mg/ml to 10 mg/ml for bathing of wounds or in-dwelling devices.

A vaccine composition is conveniently in injectable form. Conventional adjuvants may be employed to enhance the immune response.

A suitable unit dose for vaccination is 0.5–5 mg/kg of antigen, and such dose is preferably administered 1–3 times and with an interval of 1–3 weeks.

With the indicated dose range, no adverse toxicological effects will be observed with the compounds of the invention which would preclude their administration to suitable individuals.

The antibodies described above may also be used as diagnostic reagents to detect the presence of bacteria containing the response regulator protein of the invention.

EXAMPLES

The present invention is further described by the following examples. These exemplification's, while illustrating certain specific aspects of the invention, do not portray the limitations or circumscribe the scope of the disclosed invention.

Certain terms used herein are explained in the foregoing glossary.

All examples were carried out using standard techniques, which are well known and routine to those of skill in the art, except where otherwise described in detail. Routine molecular biology techniques of the following examples can be carried out as described in standard laboratory manuals, such as Sambrook et al., cited above.

Example 1

Isolation of DNA coding for a Novel Response Regulator Protein from S. Aureus WCUH 29

The polynucleotide having the DNA sequence given in SEQ ID NO: 1 was obtained from a library of clones of chromosomal DNA of S. aureus WCUH 29 in E. coli. Libraries may be prepared by routine methods, for example: Methods1 and 2

Total cellular DNA is isolated from Staphylococcus aureus strain WCUH29 (NCIMB 40771) according to standard procedures and size-fractionated by either of two methods.

Method 1.

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and E. coli infected with the packaged library. The library is amplified by standard procedures.

Method 2.

Total cellular DNA is partially hydrolysed with a combination of four restriction enzymes (RsaI, PalI, AluI and Bsh1235I) and size-fractionated according to standard procedures. EcoRI linkers are ligated to the DNA and the fragments then ligated into the vector Lambda ZapII that have been cut with EcoRI, the library packaged by standard procedures, and E. coli infected with the packaged library. The library is amplified by standard procedures.

The sequences of the novel compounds are provided in FIGS. 1 and 2, SEQ ID NOs:1 and 2. The amino acid sequence of SEQ ID NO:2 is the translated open reading frame of SEQ ID NO:1. The open reading frame is in the reverse orientation, with the start at nucleotide 759 and the end at nucleotide 58 of SEQ ID NO:1. SEQ ID NO:2 displays homology (37% identity) to the PhoP regulatory protein from Bacillus subtilis.

What is claimed is:

1. An isolated, recombinant DNA comprising the sequence fully complementary to nucleotides 1 to 850 set forth in SEQ ID NO:1.

2. An isolated, recombinant DNA comprising the sequence fully complementary to nucleotides 58 to 759 set forth in SEQ ID NO:1.

3. An isolated, recombinant DNA which encodes a polypeptide comprising amino acids 1 to 233 set forth in SEQ ID NO:2.

4. A vector comprising the DNA of claim 3.

5. An isolated host cell comprising the vector of claim 4.

6. A process for producing a polypeptide comprising; expressing from the host cell of claim 5 a response regulator encoded by said DNA.

7. A process for producing a cell which expresses a response regulator comnprising transforming or transfecting the cell with the vector of claim 4 such that the cell expresses the response regulator encoded by the cDNA contained in the vector.

8. An isolated RNA comprising an RNA sequence encoding the polypeptide sequence of SEQ ID NO:2.

9. An isolated RNA consisting of an RNA sequence transcribed from nucleotides 58 through 759 of SEQ ID NO:1.

10. An isolated polynucleotide segment, comprising a first polynucleotide sequence, wherein the first polynucleotide sequence is selected from the group consisting of:

(a) a first sequence having the polynucleotide sequence set forth in SEQ ID NO:1;

(b) a second sequence having nucleotides 1 to 850 of the polynucleotide sequence set forth in SEQ ID NO:1;

(c) a third sequence having nucleotides 58 to 759 of the polynucleotide sequence set forth in SEQ ID NO:1;

(d) a fourth sequence having at least 30 sequential bases of the polynucleotide sequence set forth in SEQ ID NO:1;

(e) a fifth sequence having at least 50 sequential bases of the polynucleotide sequence set forth in SEQ ID NO:1; and (f) the frill complement of the entire length of the polynucleotide sequence of (a), (b), (c), (d) or (e).

11. The isolated polynucleotide segment of claim 10, wherein the isolated polynucleotide segment is DNA.

12. A vector comprising the DNA of claim 11.

13. An isolated host cell comprising the vector of claim 12.

14. A process for producing a polypeptide of the first polynucleotide sequence comprising the step of culturing the host cell of claim 13 under conditions sufficient for the production of said polypeptide, which is encoded by the first polynucleotide sequence.

15. The isolated polynucleotide segment of claim 10, wherein the first polynucleotide sequence consists of a sequence having at least 30 sequential bases of the polynucleotide sequence set forth in SEQ ID NO:1.

16. The isolated polynucleotide segment of claim 10, wherein the first polynucleotide sequence consists of a sequence having at least 50 sequential bases of the polynucleotide sequence set forth in SEQ ID NO:1.

17. An isolated polynucleotide segment, comprising a first polynucleotide sequence, wherein the first polynucleotide sequence encodes a polypeptide sequence selected from the group consisting of:

(a) the sequence set forth in SEQ ID NO:2;

(b) a portion of SEQ ID NO:2 containing at least 30 amino acids; and (c) a portion of SEQ ID NO:2 containing at least 50 atino acids;

wherein the polypeptide sequence is capable of generating antibodies having binding specificity for the amino acid sequence set forth in SEQ ID NO:2.

18. The isolated polynucleotide segment of claim 17, wherein the isolated polynucleotide segment is DNA.

19. A vector comprising the DNA of claim 18.

20. An isolated host cell comprising the vector of claim 19.

21. A process for producing a polypeptide of the first polynucleotide sequence comprising the step of culturing the host cell of claim 20 under conditions sufficient for the production of said polypeptide, which is encoded by the first polynucleotide sequence.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 850 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO:1:

```
AATGCACTAA ATAAAATAAC CGTAATGGAA TAAATCGCAA TTCTAGCATA GAGTGTTTTA      60
AACATGATTC TCCACCTTAT AGCCTTGTCC TCTTACTGTG TCAATTGTAA GTGTGGCATT     120
TAATTTTTTT AATCTTTGGC GTAGTCGCTT AATATGAACG TCAACTGTTC GTTCATCTCC     180
TTCATAATCA TAGCCCCAAA TTTTTTCTAT TATTTGTTCA CGAGTAAAGA TTTGCTTAGG     240
ACGTGCTGCA AGCATAAATA ATAATTGAAA TTCCTTGTTC GGTAACGTCA TCGTTTTATT     300
AGATACTTGG AGTTCCAAAT AGGATTGGTT TAGCGTTAAG TTGCCAATAG TCATTTCTGA     360
ATTTGAATTG ATATTATATC GACGTAATAC CGCACGANTT CTAAAAATAA GTTCCTTAAC     420
CTCAAAGGGT TTGGTTACAT AATCGTCAGT ACCACTTATA AACGCACGCT CTTTGTCACT     480
AAGTGCATCC CGCGCTGTTA ACATAATAAC TGGTATATCA TAATCATTTT TTAATGTATT     540
ACATAATTGA AAGCCGTCCA TACCATCCAT CATAATATCT ACCACTGCAA TATCGACACG     600
CTGTTTTTCT AAAAGTTTTA ATGCAGCTTC ACCACTTGGT TGTGTGTATG CATCAATGTG     660
CTCTGTTTGT AAATGGCTAG CTATATAATT TAGGATTCGA GGATCGTCAT CGACAACAAG     720
ACATTGCACC ATAGCTATAA ACTCCCTTAT CTTTTTCATT TATTATACAT GTAAAATATT     780
TTTGGGTAAA AAAACAATGG TTCATATTGA GTTCATATTT CAACCCTTAT ACTTGACGCT     840
AAAGAAGAAA                                                            850
```

(2) INFORMATION FOR SEQ ID NO:2:

(i) SEQUENCE CHARACTERISTICS:
      (A) LENGTH: 233 amino acids
      (B) TYPE: amino acid
      (C) STRANDEDNESS:
      (D) TOPOLOGY: linear (ii) MOLECULE TYPE: protein (xi) SEQUENCE DESCRIPTION: SEQ ID NO:2:

```
Met Lys Lys Ile Arg Glu Phe Ile Ala Met Val Gln Cys Leu Val Val
1               5                   10                  15

Asp Asp Asp Pro Arg Ile Leu Asn Tyr Ile Ala Ser His Leu Gln Thr
            20                  25                  30

Glu His Ile Asp Ala Tyr Thr Gln Pro Ser Gly Glu Ala Ala Leu Lys
        35                  40                  45

Leu Leu Glu Lys Gln Arg Val Asp Ile Ala Val Val Asp Ile Met Met
    50                  55                  60

Asp Gly Met Asp Gly Phe Gln Leu Cys Asn Thr Leu Lys Asn Asp Tyr
65                  70                  75                  80

Asp Ile Pro Val Ile Met Leu Thr Ala Arg Asp Ala Leu Ser Asp Lys
                85                  90                  95
```

```
Glu Arg Ala Phe Ile Ser Gly Thr Asp Asp Tyr Val Thr Lys Pro Phe
            100                 105                 110

Glu Val Lys Glu Leu Ile Phe Arg Ile Arg Ala Val Leu Arg Arg Tyr
        115                 120                 125

Asn Ile Asn Ser Asn Ser Glu Met Thr Ile Gly Asn Leu Thr Leu Asn
    130                 135                 140

Gln Ser Tyr Leu Glu Leu Gln Val Ser Asn Lys Thr Met Thr Leu Pro
145                 150                 155                 160

Asn Lys Glu Phe Gln Leu Leu Phe Met Leu Ala Ala Arg Pro Lys Gln
            165                 170                 175

Ile Phe Thr Arg Glu Gln Ile Ile Glu Lys Ile Trp Gly Tyr Asp Tyr
            180                 185                 190

Glu Gly Asp Glu Arg Thr Val Asp Val His Ile Lys Arg Leu Arg Gln
        195                 200                 205

Arg Leu Lys Lys Leu Asn Ala Thr Leu Thr Ile Asp Thr Val Arg Gly
    210                 215                 220

Gln Gly Tyr Lys Val Glu Asn His Val
225                 230
```